US00PP10374P

United States Patent [19]

Barnhoorn

[11] Patent Number: Plant 10,374

[45] Date of Patent: May 5, 1998

[54] HIPPEASTRUM (AMARYLLIS) PLANT NAMED 'DOUBLE SIX'

[75] Inventor: Andre Barnhoorn, Wilgespruit, South Africa

[73] Assignee: Hadeco (Pty.) Ltd., Maraisburg, South Africa

[21] Appl. No.: 672,944

[22] Filed: Jul. 1, 1996

[51] Int. Cl.[6] ..... A01H 5/00

[52] U.S. Cl. ..... Plt./68.1

[58] Field of Search ..... Plt./68.1, 87.4

[56] References Cited

U.S. PATENT DOCUMENTS

P.P. 6,205 6/1988 Amemiya ..... Plt./68.1

OTHER PUBLICATIONS

UPOV ROM Disk 1997/01 Search Report, 1997.

*Primary Examiner*—Howard J. Locker

*Assistant Examiner*—Kent L. Bell

*Attorney, Agent, or Firm*—C. A. Whealy

[57] ABSTRACT

A distinct cultivar of Hippeastrum (Amaryllis) plant named, 'Double Six', characterized by its intense red flower color; consistent production of multiple flower scapes; six flowers per umbel; relatively compact plant habit; and early flowering.

1 Drawing Sheet

The present invention relates to a new and distinct cultivar of Amaryllis plant, botanically known as *Hippeastrum hybrida*, and hereinafter referred to by the cultivar name 'Double Six'.

The new cultivar is a product of a planned breeding program conducted by the inventor in Maraisburg, South Africa. The objective of the breeding program was to create new Amaryllis cultivars that were suitable for 15-cm container production, flowered quickly, with multiple flower scapes and attractive flower color.

The new cultivar originated from a cross made by the inventor of the *Hippeastrum hybrida* proprietary seedling number 25 as the male or pollen parent with the *Hippeastrum hybrida* cultivar 'Orange Sovereign' (not patented) as the female or seed parent.

The cultivar 'Double Six' was discovered and selected by the inventor ib 1986 as a flowering plant within the progeny of the stated cross in a controlled environment in Maraisburg, South Africa. Asexual reproduction of the new cultivar by double scaling st Maraisburg, South Africa, has shown that the unique features of this new Amaryllis are stable and reproduced true to type in successive generations.

The cultivar 'Double Six' has not been observed under all possible environmental conditions. The phenotype may vary somewhat with variations in environment such as temperature and light intensity, without, however, any variance in genotype. The following observations, measurements and comparisons describe plants grown in Maraisburg, South Africa, under commercial practice in a fiberglass-covered greenhouse with average day/night temperatures of 24° C. and light levels of 2,000 lux.

The following traits have been repeatedly observed and are determined to be in the unique characteristics of 'Double Six'. These characteristics in combination distinguish 'Double Six' as a new and distinct cultivar:

1. Intense red flower color that extends into the flower throat.

2. Bulbs of 28-cm in circumference will consistently produce two flower scapes per bulb. Larger bulbs will produce three scapes per bulb. Typically six flowers per umbel or scape are formed, hence the cultivar name 'Double Six'.

3. Relatively compact plant habit, appropriate for 15-cm containers.

4. Quick to flower.

'Double Six' is different from its pollen parent, the proprietary seedling number 25, in the following characteristics:

1. Plants of the cultivar 'Double Six' are 15 to 20 cm shorter than plants of the proprietary seedling number 25.

2. Plants of the cultivar 'Double Six' have more flowers per flower scape than plants of the proprietary seedling number 25.

3. The cultivar 'Double Six' will produce more flower scapes from smaller bulbs than plants of the proprietary seedling number 25.

'Double Six' is different from its seed parent, the cultivar 'Orange Sovereign' in the following characteristics:

1. Plants of the cultivar 'Double Six' are about 10 cm shorter than plants of the cultivar 'Orange Sovereign'.

2. Plants of the cultivar 'Double Six' have more flowers per flower scape than plants of the cultivar 'Orange Sovereign'.

3. Flower color of plants of the cultivar 'Double Six' is red whereas the flower color of plants of the cultivar 'Orange Sovereign' is orange.

4. The cultivar 'Double Six' will produce more flower scapes from smaller bulbs than plants of the cultivar 'Orange Sovereign'.

The accompanying colored photograph illustrated the overall appearance of the new cultivar, showing the colors as true as it is reasonably possible to obtain in colored reproductions of this type. The photograph comprises a side perspective view of a typical potted plant of 'Double Six' grown in Maraisburg, South Africa.

In the following description, color references are made to The Royal Horticultural Society Colour Chart except where general terms of ordinary dictionary significance are used. Measurements and numerical values represent averages for typical plants in 15-cm containers.

Botanical classification: *Hippeastrum hybrida* cultivar 'Double Six'.

Parentage:

*Male or pollen parent.*—*Hippeastrum hybrida* proprietary seedling number 25.

*Female or seed parent.*—*Hippeastrum hybrida* cultivar 'Orange Sovereign' (not patented).

Propagation:

*Propagation method.*—Bulbs, double scaling. Double scaling is a scaling propagation technique that utilizes two scales joined together by a section of the basal plate. To propagate using this method, bulbs are cut longitudinally into segments that include a portion of the basal plate and two oppositely-orientated scale pairs.

*Rooting habit.*—Mature bulbs are lifted (harvested) and cured with primary roots attached. After curing, bulbs are planted into containers for flowering and develop secondary roots. Thickest secondary roots are about 8 mm in diameter and light tan, 161° C., in color.

*Time to initiate secondary roots.*—14 days at 25° C. soil temperature.

Plant description:

*Form.*—Upright. At least two flower scapes develop in synchrony with a complement of five leaves.

*Plant height at flowering.*—Relatively compact plant habit, from soil level to top of flowers, about 50 cm, appropriate for 15-cm containers.

*Vigor.*—Rapid growth rate.

*Crop time.*—After planting cured bulbs, plants typically flower within five weeks.

*Foliage description.*—Leaves strap-like, simple, opposite, symmetrical, usually five in number. Midrib becomes keel-like toward leaf base. Size: Length: About 49 cm. Width: 4.5 to 5 cm. Shape: Linear. Apex: Obtuse. Margin: Entire. Texture: Smooth, glabrous. Venation pattern: Parallel. Color: Young foliage upper side: 143A. Young foliage under side: 138B. Mature foliage upper side: 137B. Mature foliage under side: 144A.

Flower description:

*Flower type and habit.*—One umbel per flower scape with six single flowers that are symmetrically arranged in a horizontal plane around the center of the umbel. Four flowers open simultaneously and the other two flowers open about seven days later. '*Natural flowering season.*—Spring.

*Flower longevity.*—At 22° C., individual flowers will last 8 days on the plant or if cut, 6 days. Flowers persistent.

*Fragrance.*—Very faint citrus-cucumber fragrance.

*Flower diameter.*—17 to 19 cm.

*Flower height.*—16 to 18 cm.

*Quantity.*—Six per umbel per flower scape. For 28-cm diameter bulbs, two scapes are typically formed. Larger bulbs produce three scapes.

*Flower buds (just before tepal separation).*—Size: Length: 9 to 13 cm. Width: 3.5 to 4 cm. Shape: Oblanceolate. Rate of opening: Typically flowers are fully open two days after tepals separate. Color: 44B.

*Tepals.*—Quantity and arrangement: Six tepals trimerous in two whorls. Shape: Five are broadly obovate and lowest tepal is oblanceolate. Tepals overlapping, but not fused. Size: Length: 12 to 16 cm. Width: Broadly obovate tepals: About 10 cm. Oblanceolate tepal: About 5 cm. Apex: Apiculate. Margin: Entire. Texture: Glabrous, smooth, pleated and satiny. Color: When opening: Upper side: 44A/44B. Throat: 46A. Under side: 43A/43B. Tube: 46A. Mature: Upper side: 44A/44B. Throat: 46A. Under side: 43A/43B. Tube: 46A. With further development, tepals darken uniformly to 46A. After senescence: 183A, dry.

*Scape.*—Aspect: Strong, erect, rigid, and upright. Length: About 41 cm. Texture: Glabrous. Color: With waxy bloom: 138C. Without waxy bloom: 145A. Base: Blush of 186C.

*Reproductive organs.*—Stamens: Six stamens appressed to lowest tepal, distal ends upwardly curved. Anthers clustered extremely close together at maturity. Anthers: Shape: Immature: Linear. Mature: Oblong. Size: Immature: About 2 mm. Mature: About 8 mm. Color: 159A. Pollen color: Approximately 162B. Pistils: Pistil number: 1. Stigma: Shape: Trilobate, each lobe recurved and light pink, 56D, on papillate surface. Style: Length: About 11 cm. Color: 41C, proximal end; 44A, distal end. Ovary number: 3-celled.

Bulb description (after harvesting and curing, before planting):

*Size.*—Diameter: About 8.9 cm. Circumference: About 28 cm.

*Color.*—With brown tunic: 164C with 166B/166C watermarks. Tunic removed: 159D.

Disease resistance: May be susceptible to Stagonospora fungi under high humidity conditions.

Seed production: Plants of the new Amaryllis typically produce seed that are about 14 mm in length, 10 mm in diameter and black in color.

It is claimed:

1. A new and distinct cultivar of Hippeastrum (Amaryllis) plant named 'Double Six', as illustrated and described.

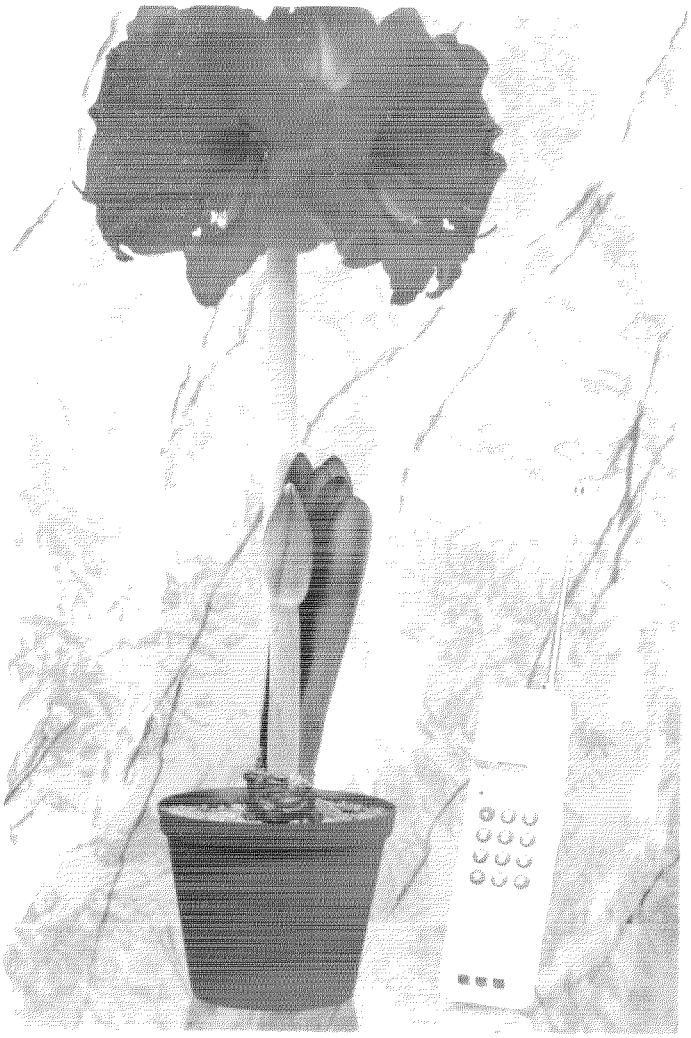

* * * * *